(12) United States Patent
Rosielle (10) Patent No.: US 8,512,353 B2
(45) Date of Patent: Aug. 20, 2013

(54) SURGICAL ROBOT

(75) Inventor: Petrus Carolus Johannes Nicolaas Rosielle, Veldhoven (NL)

(73) Assignee: Technische Universiteit Eindhoven, Eindhoven (NL)

( * ) Notice: Subject to any disclaimer, the term of this patent is extended or adjusted under 35 U.S.C. 154(b) by 1113 days.

(21) Appl. No.: 12/301,158

(22) PCT Filed: May 4, 2007

(86) PCT No.: PCT/NL2007/000117
§ 371 (c)(1),
(2), (4) Date: Dec. 31, 2008

(87) PCT Pub. No.: WO2007/133065
PCT Pub. Date: Nov. 22, 2007

(65) Prior Publication Data
US 2009/0209976 A1    Aug. 20, 2009

(30) Foreign Application Priority Data

May 17, 2006 (NL) ...................................... 1031827

(51) Int. Cl.
*A61B 17/00* (2006.01)
*A61B 19/00* (2006.01)
(52) U.S. Cl.
USPC .............................................. 606/130; 606/1
(58) Field of Classification Search
USPC .................... 606/1, 130; 74/490.01, 490.06; 318/568.11–568.16; 33/503; 600/102, 227–230
See application file for complete search history.

(56) References Cited

U.S. PATENT DOCUMENTS

| 4,527,650 | A | * | 7/1985 | Bartholet ....................... 180/8.6 |
| 6,246,200 | B1 | | 6/2001 | Blumenkranz et al. |
| 6,837,883 | B2 | * | 1/2005 | Moll et al. .................... 606/130 |
| 6,905,491 | B1 | | 6/2005 | Wang et al. |
| 7,763,015 | B2 | * | 7/2010 | Cooper et al. ................ 606/130 |
| 7,955,322 | B2 | * | 6/2011 | Devengenzo et al. ........ 606/130 |
| 2003/0135203 | A1 | * | 7/2003 | Wang et al. ................... 606/130 |
| 2004/0261179 | A1 | | 12/2004 | Blumenkranz |

FOREIGN PATENT DOCUMENTS

| EP | 0575950 | 12/1993 |
| EP | 0850632 | 7/1998 |
| WO | WO 2005/094695 | 10/2005 |

OTHER PUBLICATIONS

International Search Report for International Application No. PCT/NL2007/000117, dated Sep. 24, 2007.

* cited by examiner

Primary Examiner — Gary Jackson
Assistant Examiner — Amy Shipley
(74) Attorney, Agent, or Firm — Lumen Patent Firm (57) ABSTRACT

The present invention provides a surgical robot for performing surgery of the minimally invasive type on a body to be operated upon, which surgical robot includes a number of surgical arms having respective distal ends, to each of which distal ends a surgical instrument is connected for performing surgical procedures inside a human or animal body, a base element, manipulation means for manipulating the surgical arms relative to the base element for performing the surgery, and control means for controlling the manipulation means. Positioning means are provided for positioning the base element above the body.

10 Claims, 7 Drawing Sheets

SURGICAL ROBOT

This application is a U.S. National Stage Patent Application that claims priority to International Patent Application No. PCT/NL2007/000117 filed May 4, 2007, which in turn claims priority to Dutch Patent Application No. 1031827 filed May 17, 2006, the entireties of which are being incorporated herein by reference.

DESCRIPTION

The present invention relates to a surgical robot for performing surgery of the minimally invasive type on a body to be operated upon, which surgical robot comprises a number of surgical arms having respective distal ends, to each of which distal ends a surgical instrument is connected for performing surgical procedures inside a human or animal body, a base element, manipulation means for manipulating the surgical arms relative to the base element for performing said surgery, and control means for controlling said manipulation means.

It is known to use minimally invasive surgery (MIS) when carrying out surgical operations. When surgery of this kind is performed, access to a subcutaneous surgical site is provided via a number (typically 3 to 5) of small (typically 5-12 mm) incisions, through which a surgical arm is manually passed. The surgical arms are then coupled to the surgical robot, which is capable of manipulating the surgical arms for performing the surgical operations, such as (typically) suturing or thermally cutting through tissue and cauterizing blood vessels that have been cut through. The surgical arms thus extend through the incisions during said surgery, one of which incisions is used for supplying a gas, in particular carbon monoxide, for inflating the subcutaneous area and thus create free space at that location for manipulating the surgical instruments.

It has been found that in some cases, if not in most cases, performing MIS procedures by means of a surgical robot has advantages in comparison with manually performed MIS. Such a surgical robot comprises so-called master, which is controlled by a surgeon, and a so-called slave, being the surgical robot that performs the surgery in response to commands from the master, with a control system providing the required connection between the master and the slave. The slave robot comprises surgical arms, each configured as a long narrow bar, at the distal end of which a small instrument is provided, which instrument, just like the associated surgical arm, can be manipulated and controlled from the master. Such instruments may consist of, for example, thermal cutters, scissors, suturing tools, but also of an endoscope, by means of which the surgical site can be shown to the surgeon at the location of the master.

A surgical robot of the kind mentioned in the introduction is known from U.S. Pat. No. 6,246,200 B1. The base element of the surgical robot described therein is configured as a vertical column of at least substantially square cross-section. Said column is mounted on a kind of steel pallet, by means of which the column can be moved across the floor of an operating room. In use, the column extends beside an operating table, on which a patient to be operated upon is present. The column is provided with longitudinal guides on three of its four long sides. A manipulation arm is vertically movable along each of said longitudinal guides. A surgical arm is provided at the distal end of each of said manipulation arms, which arm is passed into the body to be operated upon via an incision and which is provided with surgical instruments at the distal ends, i.e. in the case of percutaneous surgery, for performing a surgical procedure. Each of the manipulation arms is of constructionally complex design, with a large number of degrees of freedom, and in addition said manipulation arms are comparatively heavily dimensioned in connection with the required precision at the location of the percutaneous surgical site. In addition to that, comparatively large movements of the arm parts of which each manipulation arm is made up may be required even for effecting comparatively small movements by the surgical instruments at the location of the surgical site. Because of its size and unwieldiness, the known surgical robot not only has the disadvantage of a substantial cost price, but also of being heavy and difficult to manoeuvre, for example for optimally positioning the surgical robot with respect to a patient prior to surgery, and that moreover, and perhaps even more importantly, the surgical robot of necessity takes up a great deal of space in the direct vicinity of a patient, so that only a limited amount of space remains for surgeons or other surgical staff in the direct vicinity of the patient.

U.S. Pat. No. 6,905,491 B1 describes another surgical robot. With said surgical robot, the operating table on which a patient is present basically functions as the base element. Three manipulation arms are mounted side-by-side to the operating table on the longitudinal side thereof. In this case, too, the three manipulation arms positioned side-by-side take up a significant amount of space, thereby limiting the freedom of movement of staff around the operating table. In addition, the manipulation arms, which are of identical construction, are of comparatively complex design.

US patent application US 2004/0261179 A1 describes a surgical robot comprising three individual manipulation arms, which are each individually suspended from the ceiling of an operating room above an operating table. The manipulation arms are comparatively large, heavy, unwieldy and of complex construction. In addition, said manipulation arms take up a great deal of space above the operating table, where space must also be made available for other equipment such as surgical lamps and display screens.

As an aside it is noted that International patent application WO 2005/094695 A1 describes a surgical retractor. Such a surgical retractor is used in preparing external surgery for providing the surgeon access to the operating field. The surgical retractor in question comprises a ring-shaped frame, which is positioned over an operating field by means of arms that can be manipulated relative to the frame, from the ends of which arms quarter-cylindrical retractor blades extend downwards. In use, a surgeon makes an incision in the patient's skin, whereupon the retractor blades can be inserted into the incision and be moved apart so as to enlarge the opening formed by the incision and enable the surgeon to inspect the operating field through the incision and perform manual surgery, with the ring-shaped frame providing a working support for the surgeon to rest his/her hands or arms thereon. The surgical retractor itself is not used for performing surgery therewith, but only for providing an access opening in the body for manually performing an external surgical procedure.

The object of the present invention is to provide a solution for the above-mentioned problems, or at least an improvement in that regard. In order to achieve that object, the surgical robot according to the invention is characterised in that positioning means are provided for positioning the base element above the body. Positioning the base element above the body by the positioning means has quite significant advantages. Thus, the manipulation means, such as manipulation arms by means of which the surgical arms are manipulated, may be of relatively small and lightweight construction, on account of the comparatively limited distance between the base element and the body to be operated upon. Because of this advantageous characteristic of the manipulation means, its driving mechanism can also be relatively light in weight. The limited distance between the base element and the body further helps to ensure that the manipulation of the surgical instruments in the body for performing surgery can take place with great precision. Another important advantage is the fact that the specific position of the base element makes it possible to realise a relatively compact design of the positioning means, so that said positioning means will take up little space and provide a relatively great freedom of movement for surgical staff around the body to be operated upon, leaving relatively much space for other equipment, such as surgical lamps and display screens above the operating table.

In a greatly preferred embodiment, the positioning means comprise locking means for temporarily locking the base element in a specific spatial position and orientation. In this way the base element can constitute a highly reliable and precise reference body, from where the movements of the surgical arms are carried out.

For constructional reasons it is preferable in that case if the positioning means comprise a column so as to enable vertical adjustment of the base element, in which case it is furthermore preferably if said column is either of the telescopic type, so as to enable vertical adjustment of the base element through telescoping movement of the column, or comprises a longitudinal guide for guiding the base element therealong, without excluding any other ways of realising vertical movement of the base element for that matter. A significant advantage of the vertical adjustability of the base element is that it is possible to realise an optimum height of the base element above the body to be operated upon for each individual patient.

To enable adjustment of the position of the base element in a body's longitudinal direction, normally corresponding to the longitudinal direction of an operating table, it is quite preferable if the column is pivotable about a pivot axis parallel to the longitudinal direction of the column and/or if the positioning means are provided with a horizontal guide for guiding the column in horizontal direction, preferably parallel to the longitudinal direction of the body, along the body.

According to another important preferred embodiment, the positioning means comprise a horizontally extending supporting arm, to which the base element is mounted and which is coupled to the column. Thus it is possible to arrange the positioning means so that they extend over the body to be operated upon, as it were.

The base element is preferably mounted to one end of the supporting arm in that case, so that optimum use is made of the material of the supporting arm.

Furthermore preferably, the base element is mounted to the supporting arm via a lateral surface of the base element. This makes it possible to make the supporting arm as short and thus as light in weight as possible, whilst in addition the joint height of the base element and the supporting arm also remains within bounds, since there is at least a partial and preferably a complete overlap in vertical direction.

To provide further degrees of freedom in the horizontal plane, it is furthermore preferable if the supporting arm is movable in a direction perpendicular to the longitudinal direction of the column and/or if the supporting arm is pivotable about a pivot axis parallel to the longitudinal direction of the column.

To obtain a short force loop and thus achieve a high degree of precision, the positioning means are preferably coupled to a support for the body. Generally, an operating table will function as said support. The horizontal guide used in a previously discussed preferred embodiment, is furthermore preferably mounted to the support in that case.

To achieve a larger degree of freedom with regard to mounting equipment to the base element, the base element is preferably at least substantially polygonal in shape, seen in plan view. Each side of the polygonal shape may lend itself for mounting a piece of equipment thereto. Such a piece of equipment might be a supporting arm and/or manipulation arms provided with associated surgical arms for the various surgical instruments.

A similar advantage may furthermore apply if, according to another preferred embodiment, the base element is rotationally symmetrical in shape, at least in plan view.

Possibly in combination with the polygonal shape, another preferred embodiment is characterised in that the base element is curved, preferably kidney-shaped, at least in plan view, with the surgical arms extending towards the inner side of the curvature. Thus, the surgical arms can extend in radially inward direction towards a surgical site from more or less the same base, with the base being positioned at a location not directly above the surgical site.

According to a very important preferred embodiment, the manipulation means comprise at least one manipulation arm to be driven by drive means for each surgical arm, which manipulation arm is on the one hand connected to the base element and which on the other hand engages an associated surgical arm at an upper point of engagement. Because of the main aspect of the invention, said at least one manipulation arm may be comparatively small.

An easy but nevertheless stable manipulation of the surgical arms can take place in particular if two manipulation arms defining a V-shape between them are provided, with the upper point of engagement being located in the point of the V-shape. Since the two manipulation arms can be controlled individually, two degrees of freedom become available for manipulating the associated surgical arm.

Said at least one manipulation arm preferably extends rectilinearly between the base element and the surgical arm, wherein the length of the manipulation arm can be adjusted by activating the drive means. The possibility of changing the length of the manipulation arm may be constructionally realised by using a telescopic arm, for example. Such a manipulation arm may be generally referred to as a "bar-type actuator" (BTA).

Alternatively it is also conceivable within the framework of the invention that said at least one a manipulation arm comprises an articulated arm with two arm parts that are pivotally about a first pivot axis interconnected, a proximal arm part of which pivotally about a second pivot axis engages the base element upon being driven by drive means and a distal arm part of which engages the surgical arm. It is also conceivable in that connection that one arm part is configured as a telescopic arm part.

To increase the number of available degrees of freedom, it may furthermore be advantageous if further drive means are provided for pivoting the two arm parts relative to each other.

Another special embodiment is characterised in that the first pivot axis and the second pivot axis intersect at a point of intersection located at a longitudinal position of the surgical arm. Quite preferably, the longitudinal position in question is eventually located at the incision where the surgical arm in question enters the body. Pivoting about the first pivot axis, or pivoting about the second pivot axis, will not affect the position of the surgical arm at the location of the incision in that case, so that a virtual pivot point is created at the location of the incision.

A stable manipulation of the surgical arms can be achieved in particular if the manipulation means comprise at least one reference arm, which on the one hand is connected to the base element and which on the other hand engages the surgical arm at the location of a lower point of engagement located between the upper point of engagement and the distal end of the surgical arm, whilst furthermore preferably two reference arms defining a V-shape between them are provided, with the lower point of engagement being located in the point of the V-shape.

Similarly to those preferred embodiments that relate to said at least one manipulation arm, said at least one reference arm preferably extends rectilinearly between the base element and the surgical arm, wherein the length of said at least one reference arm can be adjusted by activating drive means, or wherein said at least one reference arm comprises an articulated arm comprising two pivotally interconnected arm parts, a proximal arm part of which pivotally engages the base element upon being driven by drive means and a distal arm part of which engages the surgical arm.

For reasons of constructional simplicity, the reference arms may be configured to function as passive arms while surgical operations are being performed, to which end further locking means are preferably provided for temporarily locking said at least one reference arm in a specific spatial position and orientation during manipulation of the surgical arms for performing the surgery. The reference arms may in that case be considered to be an extension of the base element, as it were. The lower point of engagement is preferably located at an incision, as a result of which said at least one reference arm contributes towards providing a (virtual) pivot point of the surgical arm at the location of the incision.

To increase the number of degrees of freedom by which the surgical arms can be manipulated, so that there will also be more possibilities for the positioning means to position the base element above the body prior to surgery, said at least one reference arm can be manipulated by drive means, and said at least one reference arms might in fact be regarded as a further manipulation arm.

The base element is preferably provided with a vertical passage, which is furthermore preferably located in the centre of the base element. This passage may be utilised for passing further pieces of equipment therethrough, for example a camera or an endoscope or other surgical instruments.

The invention will now be explained in more detail by means of a description of a preferred embodiment of the present invention, in which reference is made to the following figures.

Figure 1:
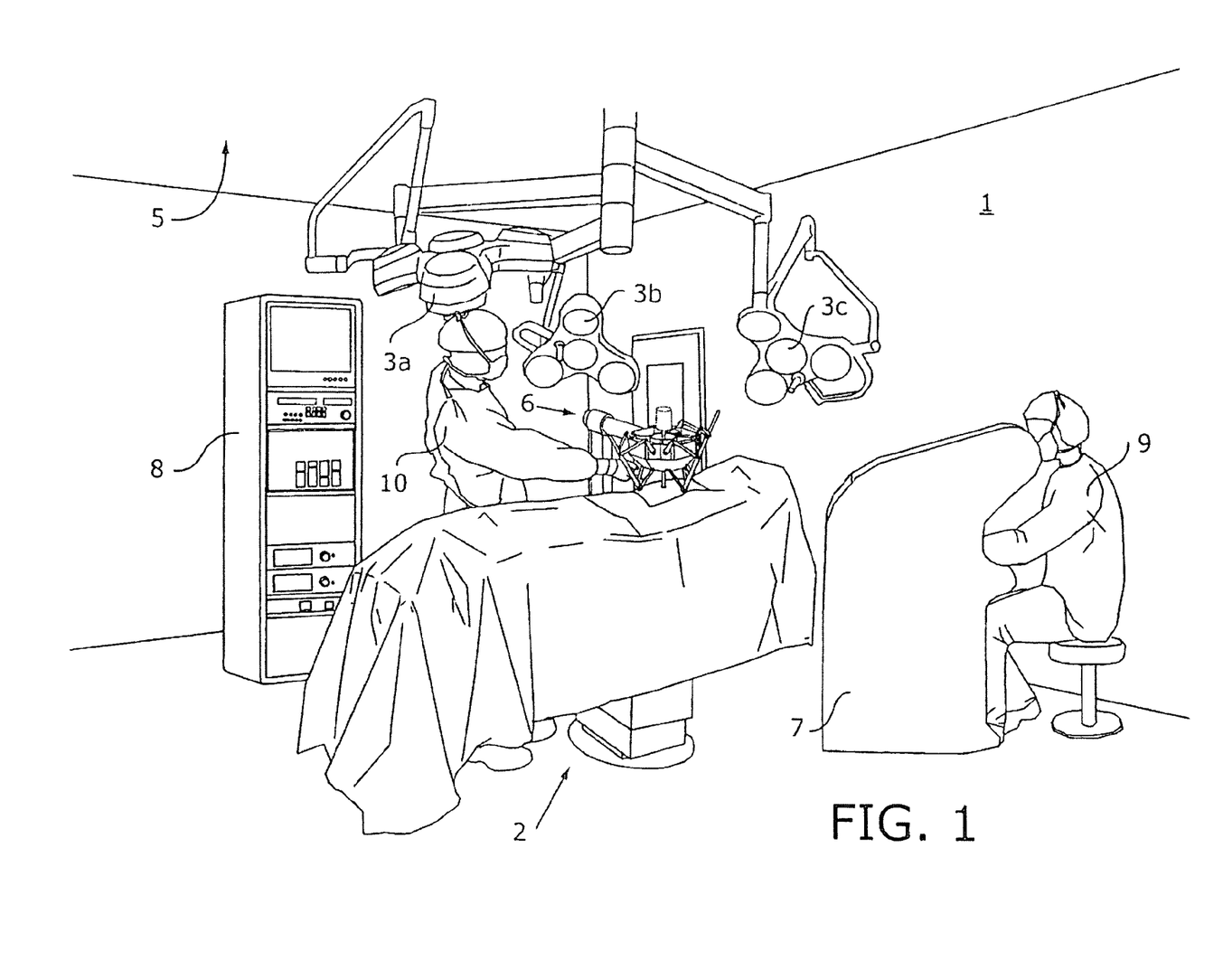
FIG. 1 shows an operating room with a surgical robot during use thereof.

Present in the operating room 1 shown in FIG. 1 is an operating table 2, above which three lighting units 3a, 3b, 3c are adjustably suspended from the ceiling 5 of the operating room 1 via a system of arms 4. Furthermore present in the operating room 1 is a telesurgery system comprising a surgical robot 6, a control console 7 and a control system 8. The surgical robot 6 may also be referred to as the "slave", whilst the control console 7 may be referred to as the "master". Via the control console 7 the surgeon 9, assisted in the operating room 2 by an assistant 10, can control the surgical robot 6, with the necessary software connection between the control console 7 and the surgical robot 6 being realised via the control system 8. The telesurgery can be used for performing MIS procedures on a patient lying on the operating room 2, for example in the patient's abdominal region or thorax region.

Figure 2A:
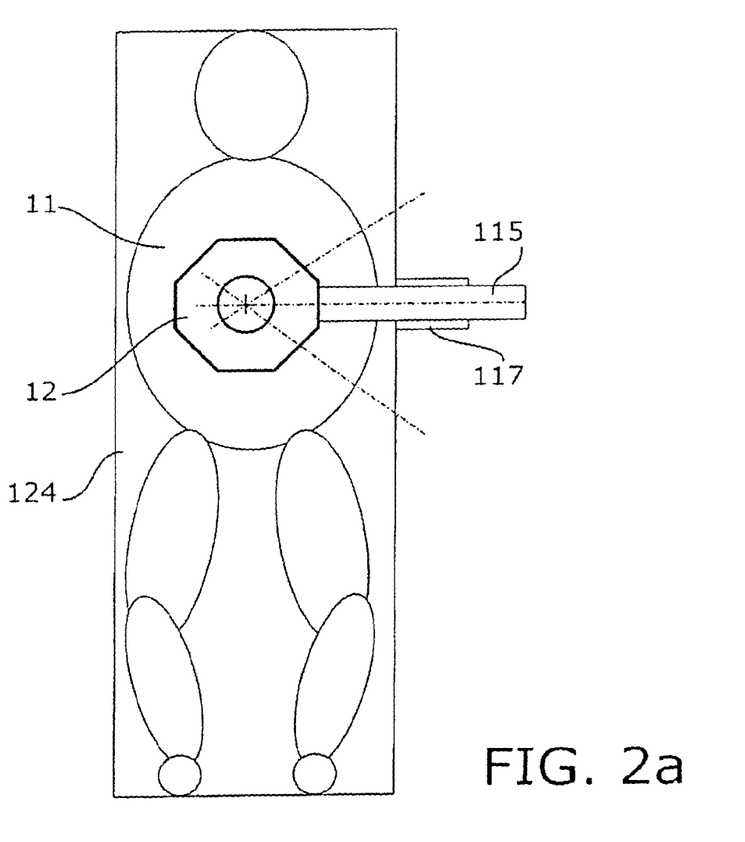
FIGS. 2a and 2b are a schematic plan view and a schematic front view, respectively, of the surgical robot of FIG. 1 with an operating table and a patient.
Figure 2B:
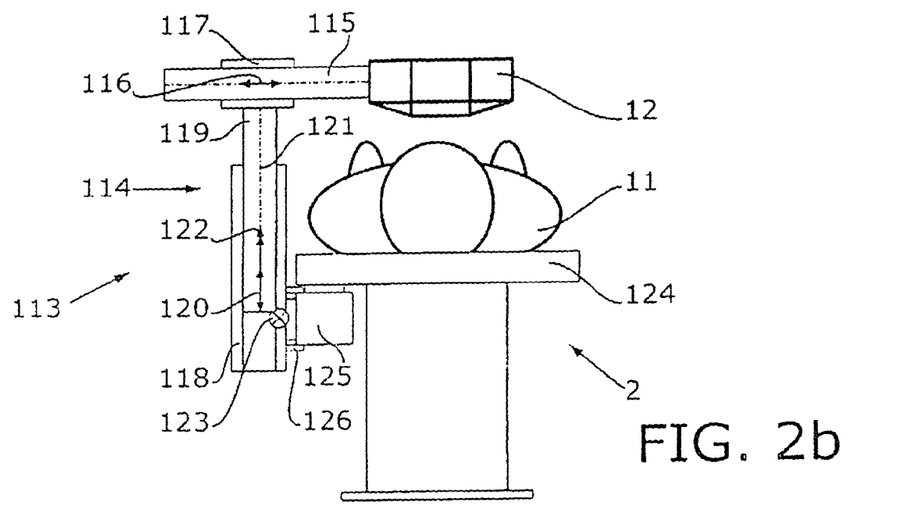

Such a patient 11 lying on the operating table 2 is shown in FIGS. 2a, 2b. In said figures, the surgical robot 6 is only shown schematically. The surgical robot 6 comprises a base element 12 provided above the patient 11. Seen in plan view, the base element 12 has an at least substantially polygonal, rotationally symmetrical shape. A frame construction 113 at least substantially consisting of a vertical, telescopic column 114 and a horizontal supporting arm 115 is provided above the patient 11 for positioning the base element 12. The base element 12 is mounted via a lateral surface thereof, which lateral surface partially defines the aforesaid polygonal shape of the base element 12. The supporting arm 115 is accommodated in a tubular guide member 117, capable of reciprocating movement therein in the directions indicated by the double arrow 116, which guide member 117 is mounted to the upper side of the column 114.

The telescopic column 114 comprises an outer, tubular telescope member 118, which accommodates an inner telescope member 119, which is capable of reciprocating motion therein in the directions indicated by the double arrow 120. In addition, the inner telescope member 119 can jointly pivot with the supporting arm 115 and the base element 12 about the central axis 121 as indicated by the arrow 122.

The frame construction 113 can be moved as a whole along the patient 11, in the longitudinal direction thereof, perpendicularly to the plane of drawing of FIG. 2b as indicated by the arrow 123, to which end a longitudinal guide 125 is provided at one longitudinal side of the operating table 2, at the bottom side of the platform 124 thereof. Said longitudinal guide 125 is capable of cooperation with guide elements 126, such as guide wheels, which are mounted to the outer telescope member 118.

The base element 12 can be optimally positioned above the patient 11 by making use of the degrees of freedom indicated by the arrows 116, 120, 122 and 123, wherein the various parts of the frame construction 113 can be moved relative to each other by manually exerting forces on controls such as handles, crank handles etc. present on or at least associated with the various parts, which can for example be done by the surgeon 9 in preparation of the surgery and subsequently by the assistant 10. On the other hand, the possibility of adjusting the frame construction 113 by means of electric motors or the like, possibly controlled from the control console 9, so as to position the base element 12 optimally relative to the patient 11 should not be excluded within the framework of the present invention. Once the optimum position of the base element 12 is reached, the frame construction 113 can be fixed in the adjusted position by locking the various parts of the frame construction 113 in their respective positions relative to each other. Such locking may for example take place by clamping the various parts together.

Figure 3A:
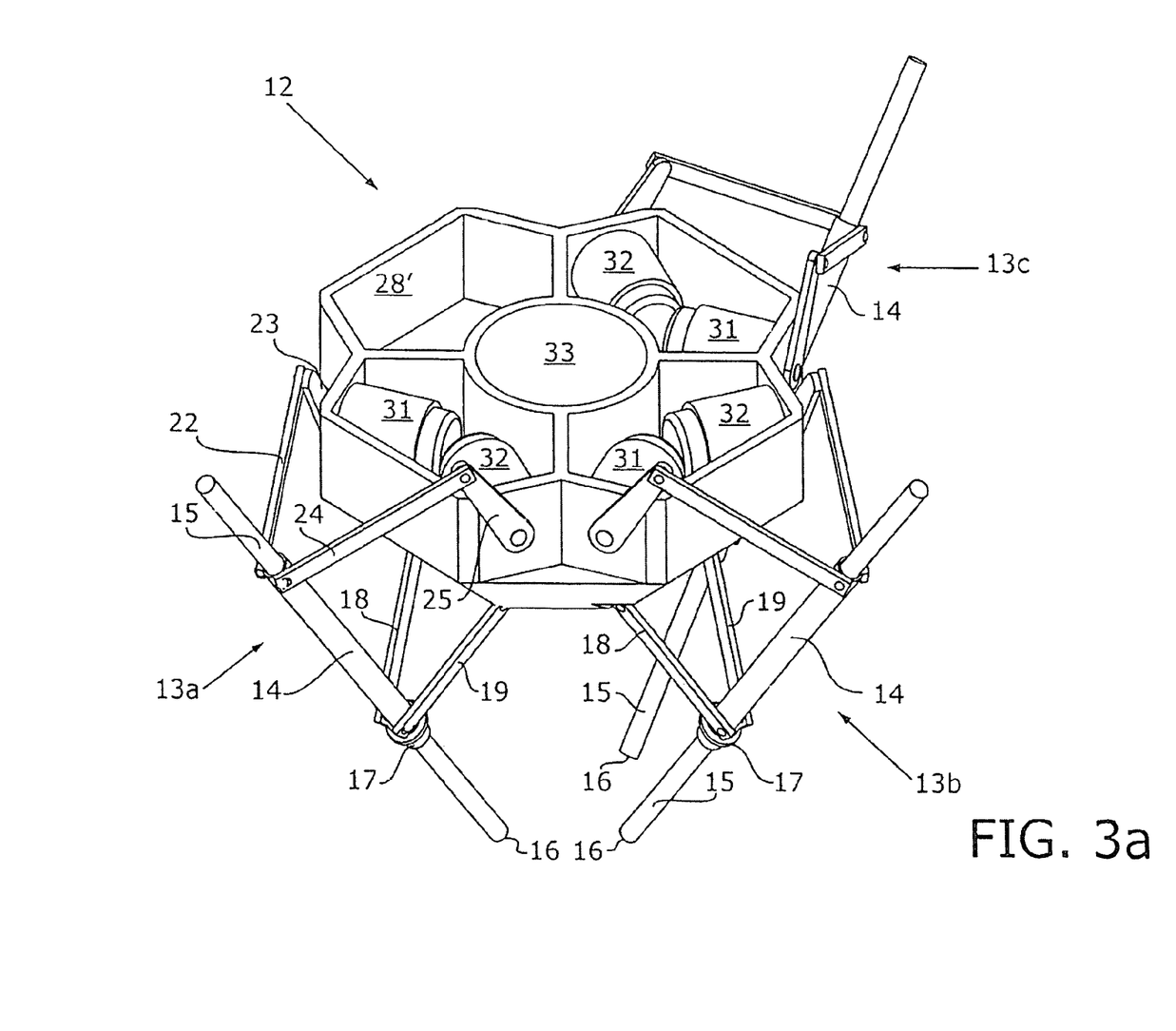
FIGS. 3a, 3b and 3c are a perspective view, a side view and a plan view, respectively, of the base element with manipulation arms and surgical arms.
Figure 3B:
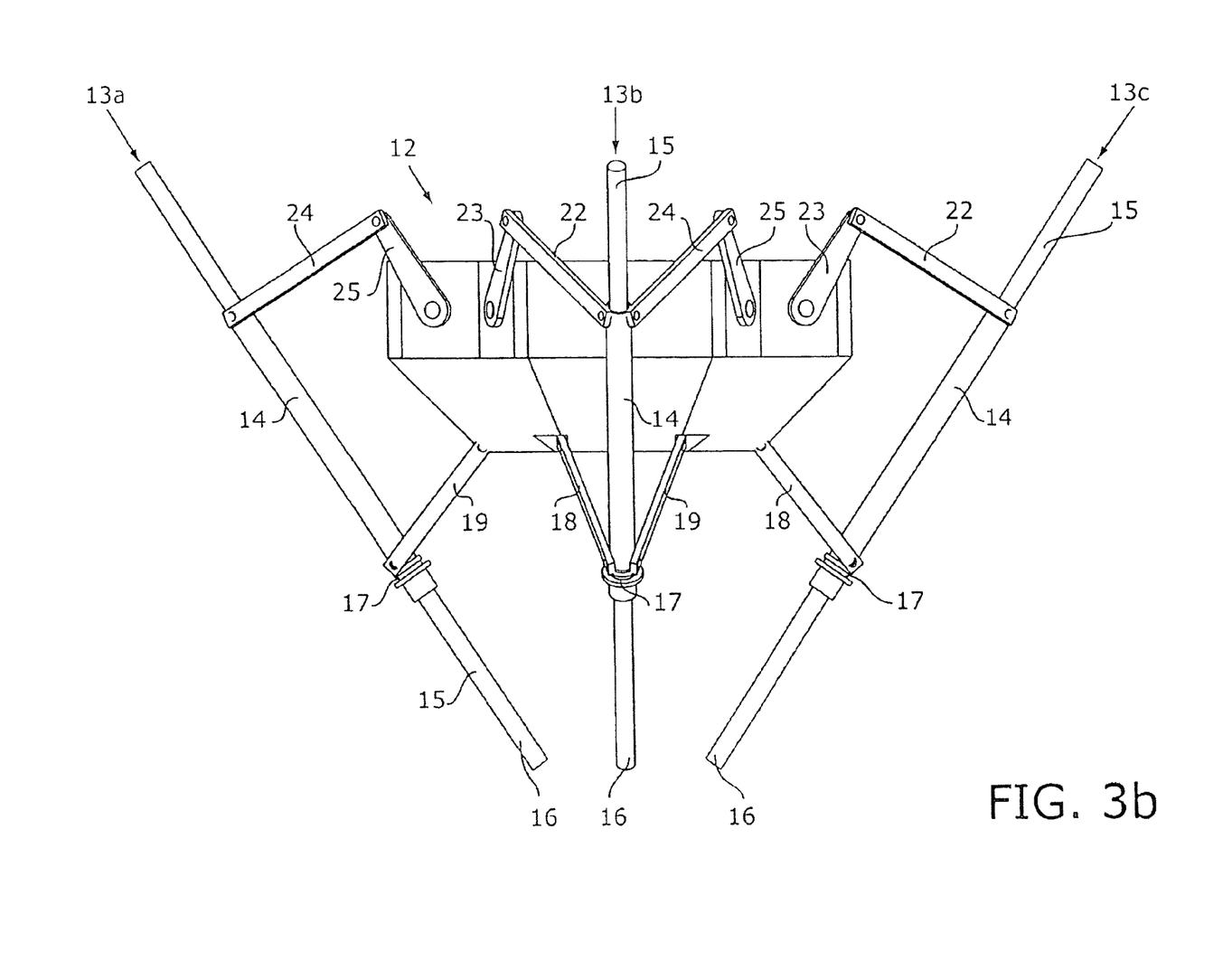
Figure 3C:
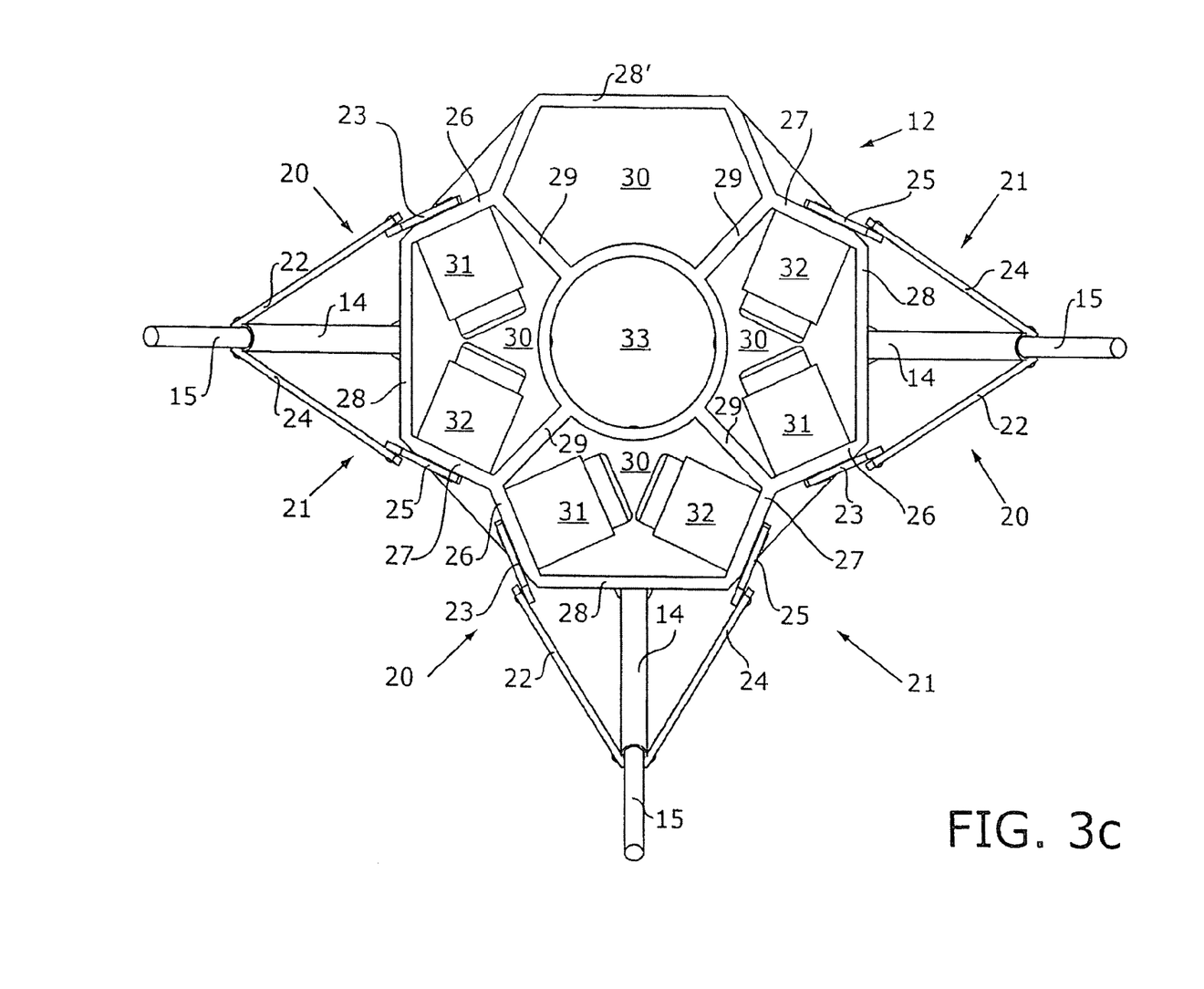

FIGS. 3a, 3b and 3c show the base element 12 provided with three surgical arms 13a, 13b, 13c (generally indicated by numeral 13) in more detail. The surgical arms 13 are basically identical to each other. For that reason no distinction will be made hereinafter between corresponding parts associated with the three surgical arms 13a, 13b and 13c as regards the reference numerals used for indicating said parts. Insofar as applicable, the letters a, b and c will be added to the numerals for referring specifically to (parts associated with) a specific surgical arm.

The surgical arms 13 comprise a fixed tubular surgical arm part 14 and an arm part 15 which is movable with respect to the fixed surgical arm part 14. The movable arm parts 15 are reciprocatingly movable in their longitudinal direction as well as rotatable about their axis within the associated fixed surgical arm parts 14. In addition to that, the movable surgical arms 15 comprise mechanisms, more specifically cardanic mechanisms, by means of which surgical instruments (not shown) mounted to the lower, distal ends 16 of the respective movable arm parts 15 can be controlled. Said controlling of the surgical instruments takes place by the surgeon 9 via the control console 7. Surgical arms, such as the surgical arms 13, are well-known to those skilled in the art. Within the framework of the present invention a more detailed explanation thereof is not considered necessary, therefore.

During an MIS procedure not only the surgical instruments need to be controlled, but in addition to that the orientation, or the inclination, of the surgical arms 13 needs to be changed. It should be realised in this connection that the surgical arms 13 enter the body of the patient 11 to be operated upon at the location of entry rings 17, also indicated by the technical term "trocars", via a small incision of about 5-12 mm. It is therefore important when changing the spatial orientation or position of the surgical arms 13 that the position of the surgical arms 13 at the location of the entry rings remains unchanged. The respective longitudinal position of the surgical arms 13 must function as a virtual (ball) joint, therefore.

To realise this situation in the constructionally simplest possible manner, two reference arms 18, 19 engage each surgical arm 13 at the location of the entry rings 17, said engagement by the reference arms 18, 19 being such that omnilateral pivoting of the surgical arms 13 relative to the reference arms 18, 19 is possible. The pairs of reference arms 18, 19 associated with a surgical arm 13 each define a V-shape, with the reference arms 18, 19 engaging the base element 12 mirror-symmetrically, at points located some distance apart, at their ends remote from the surgical arms 13. Within the framework of the invention it is also conceivable that the reference arms 18, 19 do not have the same length and/or are not arranged mirror-symmetrically, which may even be advantageous because of the greater freedom of optimally positioning/orienting the surgical arms 13 that can thus be realised. The inclination of the reference arms 18, 19 is manually set and fixed prior to an MIS procedure. If desired, it is of course also possible to have the pre-surgery adjustment of the reference arms 18, 19 carried out by a drive unit. Furthermore it is possible to make the reference arms 18, 19 interchangeable, so that for example also reference arms 18, 19 of smaller or greater length can be used, depending on the patient and on the nature of the MIS procedure to be performed.

Pairs of manipulation arms 20, 21 are provided for each surgical arm 13 for the purpose of changing the spatial orientation or the inclination of the surgical arms 13. Each manipulation arms 20, 21 is of the articulated type, comprising arm parts 22, 23 and 24, 25, which are pivotally connected. The ends of the arm parts 22, 24 engage the upper ends of the fixed surgical arm part 14 in a V-shape at a longitudinal position located some distance from the entry rings 17, with the fixed surgical arm part 14 in principle being capable of omnilateral pivoting movement relative to the arm parts 22, 24, setting aside the restrictions being imposed by the reference arms 18, 19. The arm parts 23, 25 rotatably engage the base element 12. In the present example polygonal lateral surfaces are alternately provided with V-shaped indentations, so that slightly inwardly extending lateral (half) surfaces 26, 27 are obtained for each surgical arm 13, with a full, substantially tangentially oriented lateral surface 28 therebetween. The arm parts 23, 25 extend parallel to the lateral surfaces 26, 27.

Together with two of the four radial partitions 29, the lateral surfaces 26, 27, 28 form a chamber within the base element 12, within which chamber an electric motor 31, 32 is provided for each arm part 23, 25 for rotating the respective arm parts 23, 25. Such rotation will result in spatial pivoting of the associated surgical arm 13. The electric motors 31, 32 are controlled by the control system 8 in response to control commands from the surgeon 9 at the control console 7.

FIGS. 3a and 3c furthermore clearly show a central cylindrical passage 33 provided between the chambers 30, which passage may for example be used for the provision of further lighting devices or for the passage therethrough of an additional surgical arm, for example fitted with an endoscope. It is furthermore noted that the lateral surface 28', which is a free surface in FIGS. 3a, 3b and 3c, may be used for connecting the base element to the supporting arm 115.

Figure 4A:
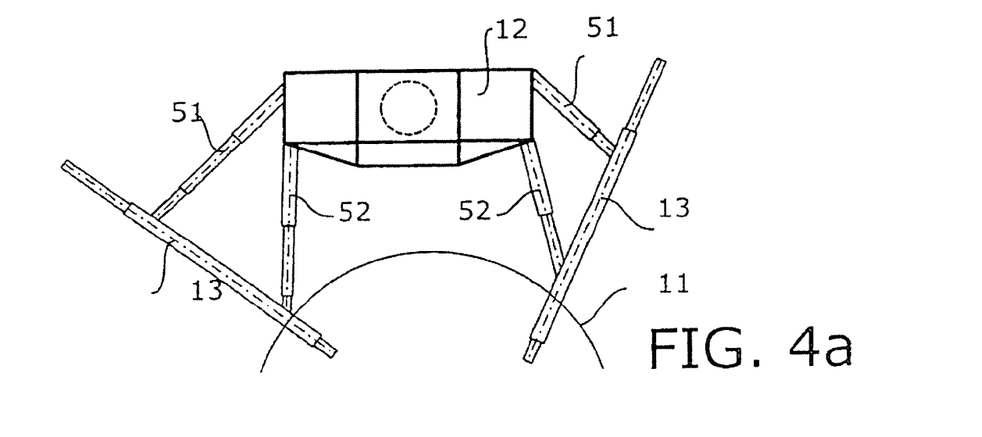
FIGS. 4a-4c are schematic side views of the base element shown in FIGS. 1, 2, and 3, in this case combined, however, with alternatively configured manipulation arms for the surgical arms.
Figure 4B:
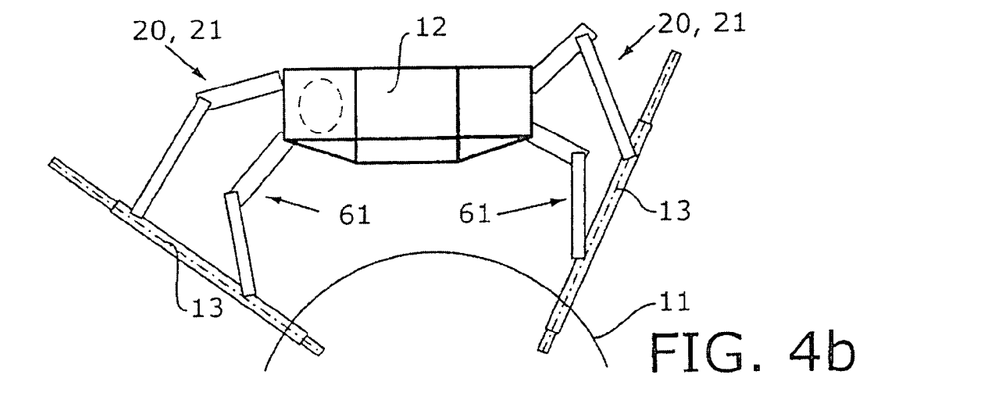
Figure 4C:
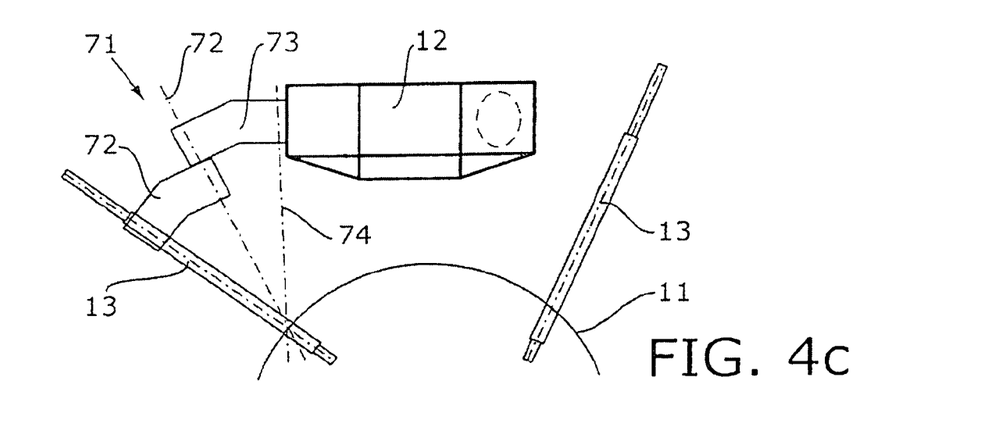

FIGS. 4a-4c show further alternative embodiments of ways in which surgical arms 13 may be manipulably connected to the base element 12. FIGS. 4a-4c furthermore schematically show part of the circumference of the patient 11 to be operated upon, which circumference can in practice be inflated by means of a gas at the location of the surgical site so as to have maximum spatial freedom inside the body of the patient 11. A broken circular line furthermore indicates a potential point of engagement for the supporting arm 115.

In the embodiment shown in FIG. 4a, the articulated manipulation arms 20, 21 as well as the rigid reference arms 18, 19 have been replaced by bar-type actuators (BTA) 51, 52, which are likewise provided in pairs defining a V-shape. Bar-type actuators may be configured as telescopic arms, for example. Typical of each of the, in total, four actuator arms 51, 52 for each surgical arm 13 is that the length thereof can be changed. In the case of the manipulation arms 51 this take place by means of drive units specially provided for that purpose, which are controlled by the control system 8. If the reference arms 52 engage the surgical arms 13 at the location of the incision, it is conceivable that the adjustment of the length of the reference arms 52 takes place manually just once. If the reference arms 52 should engage the surgical arms 13 at a position some distance away from the incision, said arms 52 would also have to be controlled actively by the control system 8 in order to ensure that the surgical arm 13 is stationary at the location of the incision during pivoting manipulation of the surgical arm 13. To that end separate drive units must be provided, of course, which drive units may form part of the base element 12, just like the motors 31, 32.

The embodiment of FIG. 4b is different from the embodiment of FIGS. 3a and 3b in that pairs of articulated further manipulation arms 61 are provided instead of the reference arms 18, 19. In FIG. 4b the lower ends of said further manipulation arms 61 engage at a position removed from the associated incisions by some distance, so that the surgeon 9 also needs to be able to control said further manipulation arms 61 via the control console 7 by using drive means separately provided for that purpose. By substituting the reference arms for manipulation arms, which will also be possible with regard to the arms 52 in FIG. 4a, a greater number of degrees of freedom is realised for the surgical arms 13, resulting in more freedom in selecting an optimum position for the base element 12.

In the embodiment of FIG. 4c, to conclude, an arm 71 made up of cranked arms 72, 73 is used as a manipulation arm for each surgical arm 13. The cranked arm 73 can rotate about the central axis 74 with respect to the base element 12. The crank arm 72 can rotate about the central axis 75 with respect to the crank arm 73. The central axes 74 and 75 intersect exactly that the point where the surgical arm 13 enters the patient's body 11. Thus, rotation of the respective arm parts 72, 73 about the axes of rotation cannot, by definition, result in an undesirable change in the position of the surgical arm 13 at the location of the incision in the skin of the patient 11.

The alternative embodiments of FIG. 4a-4c nicely illustrate how the general concept of positioning a base element over a body makes it possible to use manipulable surgical arms in various ways for performing MIS procedures. Characteristic in that connection is the fact that equipment required for manipulating the surgical arms 13 may be of comparatively simple and light construction, which may of course have an advantageous effect on the cost price of the surgical robot 6.

Figure 5A:
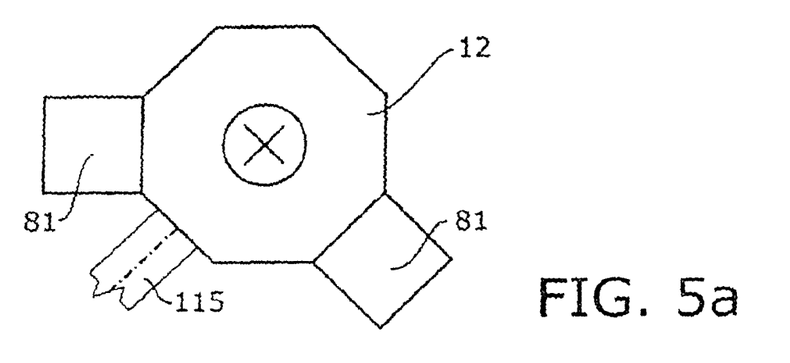
FIGS. 5a-5c are schematic plan views of alternative configurations for use with the base element.
Figure 5B:
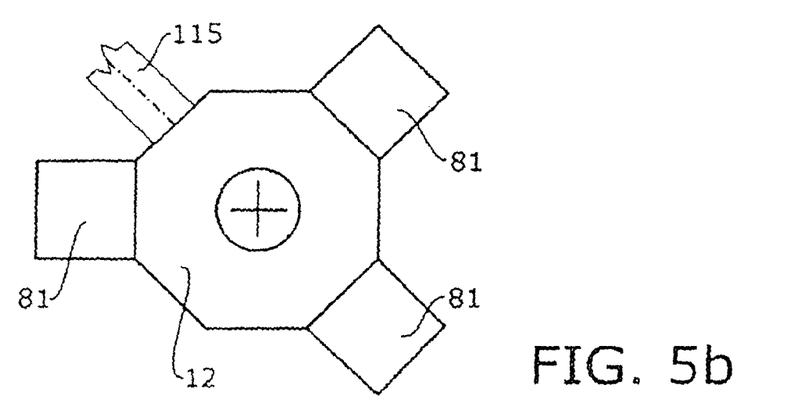
Figure 5C:
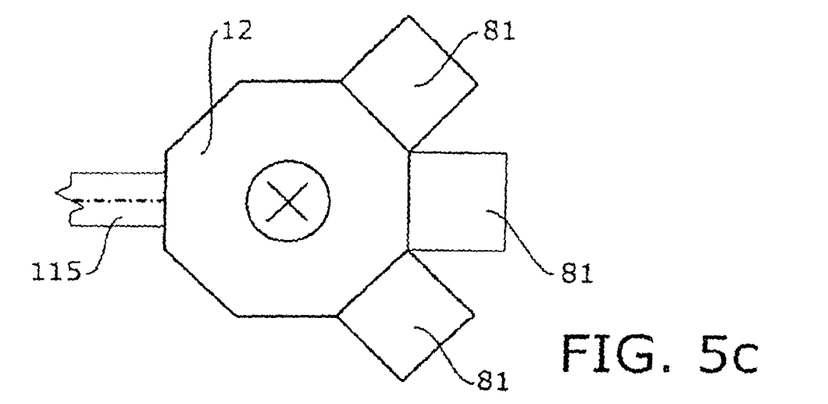

FIGS. 5a-5c finally show how, because of the polygonal and rotationally symmetrical nature of the base element 12, different configurations for the surgical robot 6 can be built up by means of modular units 81, wherein each of the (in this case) eight lateral surfaces makes it possible to mount a modular unit for a surgical arm thereto, including the manipulation means therefor, or for being connected to a fixed structure via a supporting arm 115. Each square on the outer side of the polygonal shape of the base element 12 may be regarded as such a modular unit 81.

Having perused the foregoing, it will be apparent to those skilled in the art that the present invention provides significant advantages at least with regard to the amount of space taken up by the surgical robot the constructional simplicity thereof and, connected therewith, the low cost Price. The above description of various preferred embodiments must not be construed as having a limitative effect on the present invention. Numerous variants are conceivable in that regard without departing from the inventive concept.

The invention claimed is:

1. A surgical robot for performing minimally invasive surgery, comprising:
    (a) a central base element having a transverse plane;
    (b) a surgical arm, wherein said surgical arm has a fixed surgical arm part and a movable arm part which is movable with respect to said fixed surgical arm part, wherein said fixed surgical arm part has a proximal engagement point and a distal engagement point, wherein said movable arm part has a proximal end and a distal end, wherein a surgical instrument can be mounted at said distal end of said movable arm part;
    (c) said surgical arm having two reference arms, wherein one end of each said two reference arms pivotally engages with said distal engagement point of said fixed surgical arm part and wherein another end of each said two reference arms pivotally engages with said central base element, and wherein said two reference arms define a V-shape, wherein said V-shape diverges in the direction towards said central base element and relative to said transverse plane of said base element;
    (d) said surgical arm having two manipulation arms, wherein one end of each said two manipulation arms pivotally engages with said proximal engagement point of said fixed surgical arm part and wherein another end of each said two manipulation arms pivotally engages with said central base element, wherein said two manipulation arms define a V-shape, wherein said V-shape diverges in the direction towards said central base element and relative to said transverse plane of said base element; and
    (e) said manipulation arms having a manipulation control and driving means for controlling said manipulation arms.

2. The surgical robot according to claim 1, wherein said central base element is at least substantially polygonal in shape.

3. The surgical robot according to claim 1, wherein said central base element is rotationally symmetrical in shape.

4. The surgical robot according to claim 1, wherein said cent base element is curved with said surgical arms extending towards the inner side of the curvature.

5. The surgical robot according to claim 1, wherein said at least one of said two reference arms extends rectilinearly between said central base element and said surgical arm, wherein the length of said at least one reference arm can be adjusted by activating a drive means.

6. The surgical robot according to claim 1, wherein said at least one of said two reference arms comprises an articulated arm comprising two pivotally interconnected arm parts.

7. The surgical robot according to claim 1, wherein said at least one of said two reference arms can be manipulated by drive means.

8. The surgical robot according to claim 1, wherein said central base element is movably affixed to a surgical operating table.

9. The surgical robot according to claim 1, wherein each of said manipulation arms has at least two articulated arm parts.

10. The surgical robot according to claim 1, wherein said surgical robot has a plurality of the surgical arms, wherein each of the surgical arms having the two reference arms and wherein each of said surgical arms having the two manipulation arms.

* * * * *